United States Patent
Birk et al.

(10) Patent No.: US 8,542,439 B2
(45) Date of Patent: Sep. 24, 2013

(54) METHOD AND DEVICE FOR SCANNING-MICROSCOPY IMAGING OF A SPECIMEN

(75) Inventors: Holger Birk, Meckesheim (DE); Bernd Widzgowski, Dossenheim (DE); Holger Nissle, Heidelberg (DE)

(73) Assignee: Leica Microsystems CMS GmbH, Wetzlar (DE)

( * ) Notice: Subject to any disclaimer, the term of this patent is extended or adjusted under 35 U.S.C. 154(b) by 98 days.

(21) Appl. No.: 13/347,756

(22) Filed: Jan. 11, 2012

(65) Prior Publication Data

US 2012/0175505 A1 Jul. 12, 2012

(30) Foreign Application Priority Data

Jan. 11, 2011 (DE) .......................... 10 2011 000 090

(51) Int. Cl.
*G02B 21/06* (2006.01)
*G02B 26/02* (2006.01)
*H01L 21/268* (2006.01)

(52) U.S. Cl.
USPC ................ 359/368; 359/201.1; 359/201.2; 359/362; 359/27; 250/205; 382/211

(58) Field of Classification Search
USPC ..... 359/368, 362, 27, 201.1, 201.2; 250/205; 382/211
See application file for complete search history.

(56) References Cited

U.S. PATENT DOCUMENTS

| | | | | |
|---|---|---|---|---|
| 6,771,405 B2 * | 8/2004 | Engelhardt | ................ | 359/202.1 |
| 8,031,926 B2 * | 10/2011 | Sutko et al. | ................... | 382/128 |
| 2008/0290293 A1 | 11/2008 | Motomura | | |
| 2010/0251438 A1 | 9/2010 | Huber et al. | | |

FOREIGN PATENT DOCUMENTS

| | | |
|---|---|---|
| DE | 102005045163 A1 | 3/2007 |
| DE | 102008049877 A1 | 4/2010 |
| EP | 1767979 A1 | 3/2007 |

OTHER PUBLICATIONS

Extended European Search Report from correspondent European Application 12150790.9, filed on Jan. 11, 2012, dated May 10, 2012.

* cited by examiner

*Primary Examiner* — Nikita Wells
(74) *Attorney, Agent, or Firm* — Patentbar International P.C.

(57) ABSTRACT

A method and a device for scanning-microscopy imaging of a specimen (28) are described. Provision is made that a plurality of specimen points are scanned by means of a scanning beam (14) in successive scanning time intervals, the intensity of the radiation emitted from the respectively scanned specimen point is repeatedly sensed within the associated scanning time interval, an intensity mean value is determined, as a mean value image point signal, from the intensities sensed in the respectively scanned specimen point, and the mean value image point signals are assembled into a mean value raster image. Provision is further made for additionally determining an intensity variance value, as a variance image point signal, from the intensities sensed in the respectively scanning specimen points, and for assembling the variance image point signals into a variance raster image signal.

15 Claims, 2 Drawing Sheets

METHOD AND DEVICE FOR SCANNING-MICROSCOPY IMAGING OF A SPECIMEN

RELATED APPLICATIONS

This application claims priority to German Patent Application No. DE 10 2011 000 090.9, filed Jan. 11, 2011, which is incorporated herein by reference in its entirety.

FIELD OF THE INVENTION

The invention relates to a method and a device for scanning-microscopy imaging of a specimen, according to the preamble of Claim 1 and of Claim 9, respectively.

BACKGROUND OF THE INVENTION

In scanning microscopy, especially in confocal microscopy, a specimen to be imaged is not illuminated in its entirety, but instead is scanned point by point in a raster motion by means of a scanning beam, usually emitted from a laser light source. For scanning of an individual specimen point, a scanning time interval during which the scanning beam illuminates the respective specimen point is provided. The radiation emitted from that specimen point, for example fluorescent light triggered by the scanning beam, is then sensed by a detector and converted into an image point signal. Lastly, a raster image signal is assembled from the image point signals generated for the individual specimen points, and on the basis of that signal a raster image depicting the specimen in its entirety can be presented.

The individual image point signals reproduce the brightness or intensity of the radiation that is emitted from an individual specimen point during the pertinent scanning time interval. In order to sense the radiation intensity as precisely as possible, it is conceivable for the intensity of the radiation emitted from the specimen point currently being scanned to be sensed repeatedly during the respective scanning time interval, in order then to determine an intensity mean value from the sensed intensities.

The resulting raster image signal, which reproduces the imaged specimen in its entirety, is assembled in this case from individual mean value image point signals that each represent the intensity or brightness averaged over the respective scanning time interval.

The raster images obtained in the manner described above contain exclusively the specimen brightness as image information. In order to allow, for example, dynamic processes such as diffusion to be analyzed, it would be desirable if the raster images that are generated could supply image information that goes beyond brightness.

Additional image information of this kind can be obtained, for example, in fluorescence correlation spectroscopy. With this method, however, the image information is generally sensed only for a single image point, i.e. an evaluatable raster image cannot be generated therewith. This is possible with so-called raster image correlation spectroscopy (RICS), which works with autocorrelation of the image information. With this method, however, the raster motion must occur at a speed that is in the same range as the speed with which the dynamic processes to be analyzed, for example diffusion, take place. Furthermore, evaluation with this method is particularly complex if the raster motion is not linear. Mention may also be made, in the sector of correlation spectroscopy, of an analytical method referred to in the literature as "number and brightness" (abbreviated "N&B"). This method requires multiple images in order to allow conclusions as to dynamic processes based on the fluctuation at a specific image position.

SUMMARY OF THE INVENTION

An object of the invention is to further develop a method and a device of the kind cited initially for scanning-microscopy imaging of a specimen, so as to enable simple and rapid analysis of dynamic processes on the basis of raster images.

The invention achieves this object for the method by way of the features of Claim 1, and for the device by way of the features of Claim 9.

The method according to the present invention provides for additionally determining from the intensities sensed in the respectively scanned specimen point, besides an intensity mean value that is used as a mean value image point signal, an intensity variance value as a variance image point signal, and assembling the variance image point signals thus generated for the individual specimen points into a variance raster image signal. A "specimen point" is to be understood here of course not as a point in the strictly mathematical sense, but as a spatially narrowly delimited subregion, illuminated with a focused scanning beam, of the specimen.

The invention therefore provides that for each individual specimen point that is impinged upon by the scanning beam, the intensity of the radiation emitted from that specimen point is sensed repeatedly within the associated scanning time interval, and that from those multiple intensity values both an intensity mean value and an intensity variance value is then determined For each specimen point, besides the mean brightness that is given by the intensity mean value, a further image information item in the form of the intensity variance value is therefore additionally obtained. Both the intensity mean value and the intensity variance value are used in each case as an image point signal. The image point signals generated for all the specimen points are then assembled into a mean value raster image signal and a variance raster image signal, respectively. Two raster images are generated in this fashion, namely one whose image points or pixels each represent the intensity mean value and thus the mean brightness, and another whose image points or pixels each make available a further image information item in the form of the intensity variance.

This further image information can be used to analyze dynamic processes. It can be used, for example, in fluorescence microscopy to analyze the diffusion of fluorescence dyes. On the basis of this additional image information it is also possible, depending on the application, to obtain evidence regarding viscosity fluctuations, membrane permeabilities, particle sizes, etc.

The method according to the present invention thus makes it possible to acquire two different image information items (i.e. the mean value and the variance) during irradiation of a single specimen point, and thus to generate two image points associated with that specimen point. The result of assembling those image points is thus to generate, for the same scanning beam impact on the specimen, not just one but two raster images, one reproducing the mean brightness and the other the brightness variance. The method is thus more efficient than the methods known from the existing art and cited above.

An evaluation image point signal is preferably generated on the basis of the respective mean value image point signal and the associated variance image point signal. The evaluation image point signals generated in this manner are then assembled into an evaluation raster image signal. In this advantageous refinement, an evaluation raster image is thus additionally generated, as a third image, besides the mean value raster image and the variance raster image. The three raster images can then be presented on a display apparatus in various ways, e.g. next to one another, overlaid onto one another, simultaneously, or in a predetermined image sequence, in order to facilitate the analysis of dynamic processes.

The intensity of the radiation emitted within each scanning time interval is preferably digitized n times in successive sub-intervals in order to sense n intensity values, n being a whole number greater than 1 and the sub-intervals each being equal to 1/n times the scanning time interval. For example, if the scanning time interval (often also referred to as the "pixel duration") is 10 µs, and the measurement frequency at which the intensity values are sensed within each scanning time interval is 40 MHz, then n=400 measured values are obtained for each image point or pixel. The intensity mean value and the intensity variance value are then determined on the basis of those 400 measured values.

In an advantageous embodiment, the n intensity values are sensed by the fact that an analog signal corresponding to the emitted radiation is converted by means of an analog-digital converter n times within the respective scanning time interval, in each case with a predetermined conversion time that is equal to the sub-interval, into a digital signal representing the respective intensity value. The conversion time of the analog-digital converter is thus set, in this case, to be sufficiently short that the converter can be put into operation n times within the scanning time interval in order to digitize the analog signal n times and thus sense n intensity values.

In an alternative embodiment, instead of an analog-digital converter it is possible to use a photon counter whose counting time is set to be so short that n counting cycles can be carried out within the scanning time interval.

The respective intensity mean value $\bar{x}$ is preferably determined according to formula (1) below:

$$\bar{x} = \frac{1}{n}\sum_{i=1}^{n} x_i \quad (1)$$

The respective intensity variance value V is determined according to formula (2) below:

$$V = \frac{1}{n-1}\sum_{i=1}^{n}(x_i - \bar{x})^2, \quad (2)$$

where the variable $$\sum_{i=1}^{n}(x_i - \bar{x})^2$$

is preferably determined according to formula (3)

$$\sum_{i=1}^{n}(x_i - \bar{x})^2 = \sum_{i=1}^{n} x_i^2 - n\bar{x}^2 \quad (3)$$

or according to formula (3') below:

$$\sum_{i=1}^{n}(x_i - \bar{x})^2 = \sum_{i=1}^{n} x_i^2 - \frac{1}{n}\left(\sum_{i=1}^{n} x_i\right)^2 \quad (3')$$

where
$x_i$ denotes the intensities sensed within the respective scanning time interval, and
n denotes a whole number, greater than 1, that indicates the number of intensities $x_i$ sensed within the respective scanning time interval.

As a result of the signal processing in accordance with formula (3) or (3'), both the sum, and the sum of the squares, of the intensities $x_i$ can be calculated in one pass. It is thereby possible to carry out the calculation operations directly during image acquisition, i.e. in real time during illumination of the respective specimen point with the scanning beam.

The quotient of the intensity variance value V and the intensity mean value $\bar{x}$ is preferably determined as an evaluation image point signal. This refinement can be used, for example, to sense regions of elevated diffusion in the specimen. Specifically: if it is assumed that a static specimen (i.e. one immobilized on a specimen slide) emits photons in accordance with Poisson statistics, the variance is then proportional to the number of photons emitted. This means that the mean value raster image and the variance raster image supply the same image information (leaving aside statistical fluctuations). If the photon source then additionally varies, for example, as a result of the diffusion of fluorescence dyes or the like, the variance then correspondingly increases with respect to the associated intensity mean value, i.e. with respect to the image brightness. Based on the quotient, calculated for each individual specimen point, of the intensity variance value and the intensity mean value $\bar{x}$, it is thus possible to detect regions of increased diffusion in the specimen. The evaluation image point signal calculated by way of this quotient can then be used to generate an evaluation raster image in which these regions are clearly evident.

In a further advantageous embodiment, provision is made to determine the number of photons $N_{ph}$ emitted from the respective specimen point within the associated scanning time interval, as an evaluation image point signal, as a function of the intensity mean value $\bar{x}$ and the intensity variance value V, using formula (4) below:

$$N_{ph} = \frac{\bar{x}^2}{V} \quad (4)$$

This refinement is based on the recognition that if Poisson statistics are applicable, the number of photons emitted $N_{ph}$ is given by formula (4). A determination of the number of photons $N_{ph}$ can be made independently of any gain factors and calibrations. It requires only that the Poisson noise be the dominant source of fluctuations of the measured signal, i.e. of the sensed intensity values (provided noise effects are negligible. The (inherently unknown) total gain can thus be summarized in a factor θ. In this case formula (5) below governs the number of photons $N_{ph}$:

$$\frac{N_{ph}}{\vartheta} = \bar{x}, \quad (5)$$

The Poisson statistics yield:

$$\frac{N_{ph}}{\partial^2} = V. \quad (6)$$

Lastly, the following is obtained from formulas (5) and (6):

$$\frac{\bar{x}^2}{V} = \frac{\left(\frac{Nph}{\partial}\right)^2}{\frac{Nph}{\partial^2}} = N_{ph}. \quad (7)$$

It is evident from the considerations above that the evaluation image point signal according to formula (4) is in fact suitable for determining the number of photons $N_{ph}$. In consideration of the scanning time interval, the absolute detected photon flux (e.g. in photons per second) can thus be described independently of gain factors and calibrations.

The device according to the present invention according to Claim 9 is embodied to carry out the method according to Claim 1.

In a particularly advantageous refinement of this device, the calculation unit that ascertains the respective intensity mean value and the respective intensity variance value encompasses a freely programmable logic module, in particular a field programmable gate array (FPGA), a digital signal processor (DSP), or an application-specific integrated circuit (ASIC). A logic module of this kind is capable of calculating the variables to be determined according to the present invention, namely the intensity mean value and intensity variance value, directly during image acquisition, i.e. in real time. The quantity of data that is transferred to the evaluation unit, in which the mean value image point signals are assembled into the mean value raster image signal and the variance image signals are assembled into the variance raster image signal, and those images are then evaluated, can thus be greatly reduced. For example, only the intensity mean value and the intensity variance value for each individual specimen point needs to be transferred to the evaluation unit.

BRIEF DESCRIPTION OF THE DRAWINGS

The invention will be explained below on the basis of an exemplifying embodiment with reference to the Figures, in which.

DETAILED DESCRIPTION OF THE PREFERRED EMBODIMENTS

Figure 1:
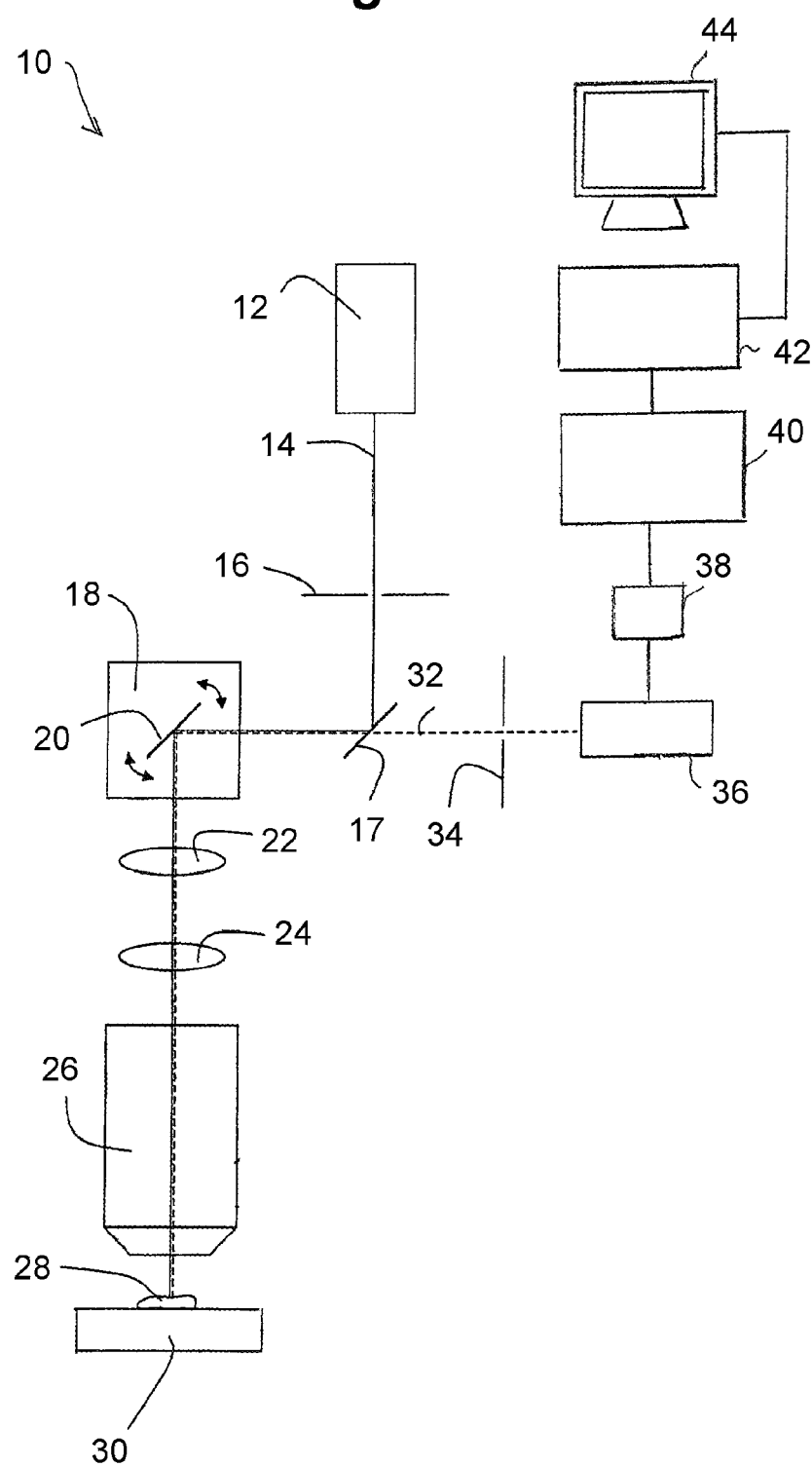
FIG. 1 shows the construction of a confocal scanning microscope according to the present invention.

FIG. 1 schematically shows a confocal scanning microscope 10 according to the present invention. Scanning microscope 10 contains a laser light source 12 that emits a scanning beam 14 onto a first aperture 16. Scanning beam 14 that passes through first aperture 16 is reflected at a stationary beam splitter 17 onto a scanning unit 18. Scanning unit 18 comprises a gimbal-mounted scanning minor 20 at which scanning beam 14 is reflected toward a scanning optical system constituted from two lenses 22 and 24. After passing through the scanning optical system, scanning beam 14 travels into an objective 26 that focuses scanning beam 14 onto a specimen 28 that is resting on a specimen stage 30. In FIG. 1, the scanning beam emitted from laser light source 12 and ultimately focused onto specimen 28 is indicated with a solid line.

Specimen 28 to be imaged is equipped with fluorescent dyes that are excited by scanning beam 14 to emit fluorescent radiation. The fluorescent radiation is indicated in FIG. 1 by a dashed line, and labeled 32. The wavelength of fluorescent radiation 32 is different from the wavelength of scanning beam 14. Fluorescent radiation 32 travels, oppositely to the propagation direction of scanning beam 14, through objective 26 and through the scanning optical system constituted by the two lenses 22 and 24. It is then incident onto scanning mirror 20, at which it is reflected toward beam splitter 17. Beam splitter 17 is embodied so that it is transparent to the wavelength of fluorescent radiation 32. Fluorescent radiation 32 thus passes through beam splitter 17 and then through a second aperture 34. A detector 36 receives the fluorescent radiation passing through second aperture 34, and converts it into a corresponding analog voltage signal.

Scanning beam 14 is focused by first aperture 16 onto specimen 28 in a manner known per se. This means that scanning beam 14 illuminates not the entire specimen 28, but instead, at least point in time, a diffraction-limited small part thereof, which in the present case will be referred to in simplified fashion as a "specimen point." This specimen point is imaged through second aperture 34 onto detector 36 in the form of a corresponding image point.

By the fact that the gimbal-mounted scanning mirror 20 is moved (as indicated by the two double arrows) by means of a drive system (not shown in FIG. 1), scanning beam 14 scans specimen 28 one specimen point at a time. A scanning time interval, during which scanning beam 14 illuminates the respective specimen point, is provided for this.

The invention now provides that during such a scanning time interval in which the respective specimen point is illuminated with scanning beam 14, the intensity of the fluorescent radiation emitted from that specimen point is to be sensed repeatedly in order to obtain multiple intensity values that are processed in a manner explained later. In the present exemplifying embodiment, multiple intensity values are sensed in each scanning time interval, by the fact that the analog voltage signal generated by detector 36 is delivered to an analog-digital converter 38. Analog-digital converter 38 converts the analog voltage signal delivered to it into a digital signal, with a conversion time that is set so that multiple analog-digital conversions are completed within the respective scanning time interval.

If it is assumed, purely by way of example, that analog-digital converter 38 operates at a frequency of 40 MHz and that the scanning time interval is equal to 10 µs, then 400 analog-digital conversions are carried out during the scanning time interval. This means that 400 digital intensity values are determined for a single specimen point.

The digital intensity values generated by the analog-digital converter are outputted to a calculation unit 40. Calculation unit 40 is, in the present exemplifying embodiment, a freely programmable logic module, for example an FPGA, DSP, or ASIC. Calculation unit 40 determines, from the digital intensity values delivered to it from analog-digital converter 38, at least two image point signals associated with the respectively scanned specimen point, namely a mean value image point signal and a variance image point signal. The determination of these two image point signals is further explained below with reference to FIG. 2.

The calculation operations needed in order to determine the two image point signals are performed by calculation unit 40 is real time, i.e. the two image point signals are available immediately after the respective scanning time interval has elapsed. Calculation unit 40 outputs the image point signals to an evaluation unit 42, e.g. a personal computer. Once all the specimen points have been scanned with scanning beam 14, a sequence of mean value image point signals and a sequence of variance image point signals (as well as sequences of further image point signals if applicable) are therefore available, which are assembled respectively into a mean value raster image signal and a variance raster image signal. Assembly to yield these raster image signals occurs, in the present exemplifying embodiment, in evaluation unit 42. With appropriate programming of calculation unit 40, however, this can also occur in the latter. Evaluation unit 42 then outputs the raster image signals to a monitor 44, on which the corresponding raster images of the imaged specimen 28 are displayed.

Figure 2:
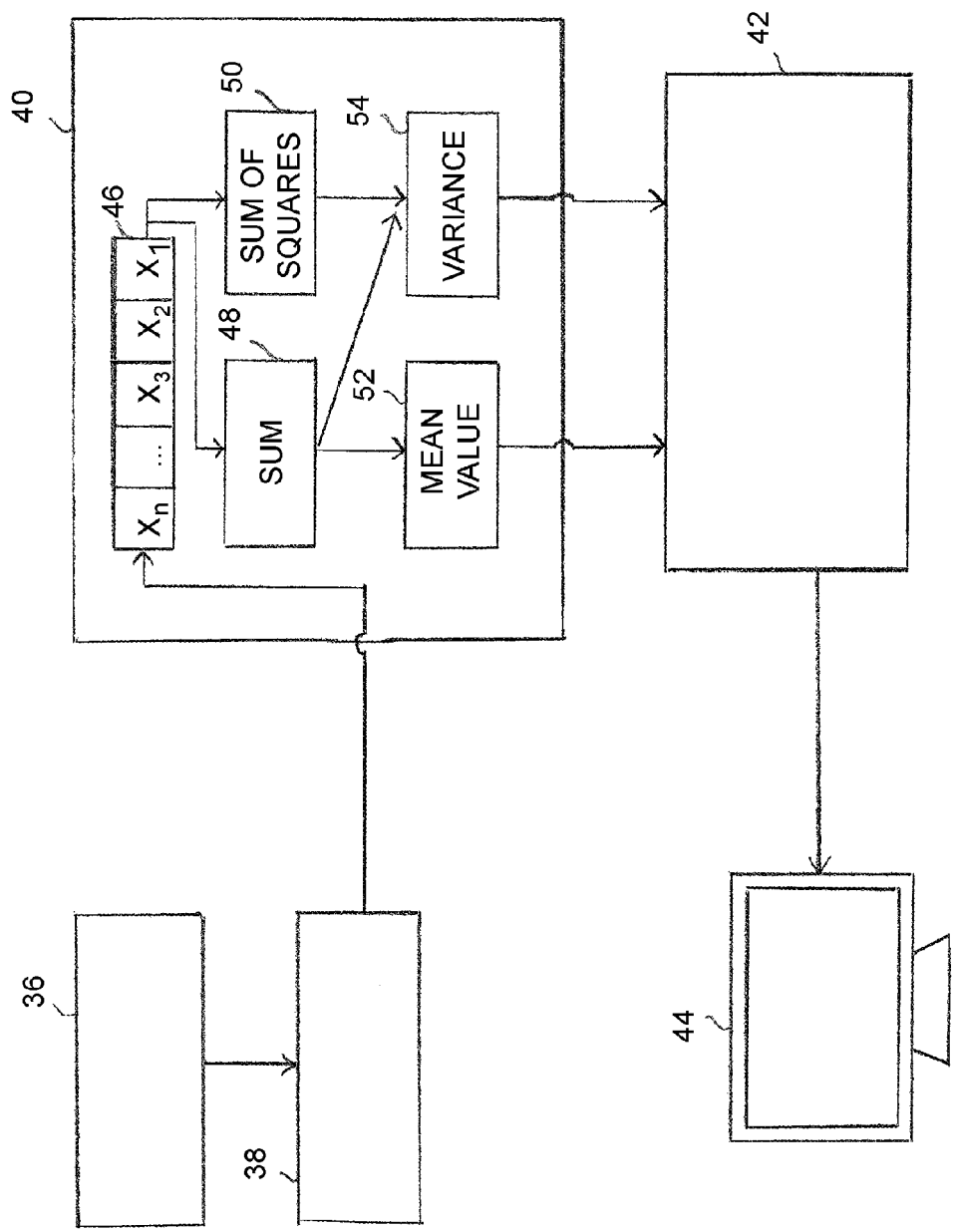
FIG. 2 shows a calculation unit provided in the scanning microscope according to FIG. 1, and the components interacting with the calculation unit.

Determination of the image point signals by calculation unit 40 will be explained in more detail below with reference to FIG. 2. For this, FIG. 2 schematically depicts an exemplifying configuration of calculation unit 40.

As already explained above, calculation unit 40 receives the digital intensity values that analog-digital converter 38 generates by converting the analog voltage signals generated, within a scanning time interval during which a respective specimen point is illuminated by scanning beam 14, by detector 36. Calculation unit 40 contains a delay element 46 to which the digital intensity values are delivered from analog-digital converter 38. Once again taking as a basis the aforementioned example in which the scanning time interval has a length of 10 μs and analog-digital converter 38 has a conversion frequency of 40 MHz, delay element 46 then receives n=400 intensity values that are labeled $x_1, x_2, x_3, \ldots x_n$ in FIG. 1. Delay element 46 performs a buffering operation on intensity values $x_1, x_2, x_3, \ldots x_n$, working on the so-called "first in, first out" principle according to which the intensity value saved first is also the first one removed again from the memory.

Delay element 46 delivers intensity values $x_1, x_2, x_3, \ldots x_n$ to a first functional block 48 and to a second functional block 50. First functional block 48 creates the sum of intensity values $x_1, x_2, x_3, \ldots x_n$, while second functional block 50 ascertains the sum of the squares of intensity values $x_1, x_2, x_3, \ldots x_n$. First functional block 48 then outputs the ascertained sum to a third functional block 52 and to a fourth functional block 54. Second functional block 50 delivers the ascertained sum of the squares to fourth functional block 54.

Third functional block 52 ascertains an intensity mean value $\bar{x}$ in accordance with formula (1) indicated earlier. Fourth functional block 54, on the other hand, ascertains an intensity variance value V utilizing formulas (2), (3), and (3') recited above. Third functional block 52 outputs the intensity mean value $\bar{x}$, as a mean value image point signal, to evaluation unit 42. Fourth functional block 54 correspondingly outputs the intensity variance value V, as a variance image point signal, to evaluation unit 42.

The above-described calculation operations of calculation unit 40 are carried out for every scanned specimen point. Once all the specimen points have been scanned with scanning beam 14, a sequence of mean value image point signals and a sequence of variance image point signals are therefore available, which are assembled in evaluation unit 42 respectively into a mean value raster image signal and a variance raster image signal. Based on these raster image signals, a mean value raster image and a variance raster image are then respectively displayed on monitor 44. Any types of image presentation are conceivable in this context. For example, the two aforementioned raster images can be displayed on monitor 44 next to one another, overlaid on each other, or successively in a predetermined time sequence. It is also conceivable to reproduce the additional image information contained in the variance raster image on monitor 44 as an overlay onto the mean value raster image in false colors, or in a three-dimensional depiction.

As discussed earlier, the additional image information contained in the variance raster image can be used in particular to analyze dynamic processes. It is conceivable, for example, to derive evidence about viscosity fluctuations, membrane permeabilities, particle sizes, diffusion parameters, etc. on the basis of this image information.

Further variables can also be determined on the basis of the intensity variance value V determined in calculation unit 40. An example that may be mentioned here is the quotient of the intensity variance value V and the intensity mean value $\bar{x}$. The number of photons $N_{ph}$ can also be ascertained in accordance with formula (7) indicated above. Based on these variables, a corresponding evaluation image point signal is then generated for each specimen point, in order then to assemble the evaluation image point signals of all the specimen points into a evaluation raster image signal, and to display the corresponding raster image on monitor 44.

The embodiment described above is to be understood as merely an example. The exemplifying embodiment shown in FIGS. 1 and 2 can thus of course be modified while retaining the approach according to the present invention. It is possible, for example, to replace detector 36 and analog-digital converter 38 with a photon counter, which senses the intensity values by sensing, in multiple counting cycles within the respective scanning time interval, the number of photons that correspond to the radiation emitted from the respective specimen point. It is furthermore self-evident that variables other than the above-described evaluation variables can also be determined on the basis of the intensity mean value and the intensity variance value.

| PARTS LIST | |
|---|---|
| 10 | Confocal scanning microscope |
| 12 | Laser light source |
| 14 | Scanning beam |
| 16 | First aperture |
| 17 | Beam splitter |
| 18 | Scanning unit |
| 20 | Scanning mirror |
| 22, 24 | Lenses |
| 26 | Objective |
| 28 | Specimen |
| 30 | Specimen stage |
| 32 | Fluorescent radiation |
| 34 | Second aperture |
| 36 | Detector |
| 38 | Analog-digital converter |
| 40 | Calculation unit |
| 42 | Evaluation unit |
| 44 | Monitor |
| 46 | Delay element |
| 48 | First functional block |
| 50 | Second functional block |
| 52 | Third functional block |
| 54 | Fourth functional block |

What is claimed is:

1. A method for scanning-microscopy imaging of a specimen (28), comprising the following steps:

scanning a plurality of specimen points by means of a scanning beam (14) in successive scanning time intervals, repeatedly sensing the intensity of the radiation emitted from the respectively scanned specimen point within the associated scanning time interval, determining an intensity mean value, as a mean value image point signal, from the intensities sensed in the respectively scanned specimen point, and assembling the mean value image point signals into a mean value raster image signal, wherein an intensity variance value is additionally determined, as a variance image point signal, from the intensities sensed in the respectively scanned specimen point, and the variance image point signals are assembled into a variance raster image signal.

2. The method according to claim 1, wherein an evaluation image point signal is generated on the basis of the respective mean value image point signal and the associated variance image point signal, and the generated evaluation image point signals are assembled into an evaluation raster image signal.

3. The method according to claim 1, wherein the intensity of the radiation emitted within each scanning time interval is digitized n times in successive sub-intervals in order to sense n intensity values, n being a whole number greater than 1 and the sub-intervals each being equal to 1/n times the scanning time interval.

4. The method according to claim 3, wherein the n intensity values are sensed by the fact that an analog signal corresponding to the emitted radiation is converted by means of an analog-digital converter n times within the respective scanning time interval, in each case with a predetermined conversion time that is equal to the sub-interval, into a digital signal representing the respective intensity value.

5. The method according to claim 3, wherein the n intensity values are sensed by the fact that the number of photons that correspond to the emitted radiation is determined by means of a photon counter n times within the respective scanning time interval, in each case with a predetermined counting time that is equal to the sub-interval.

6. The method according to claim 1, wherein the respective intensity mean value $\bar{x}$ is determined according to formula (1) below:

$$\bar{x} = \frac{1}{n}\sum_{i=1}^{n} x_i \quad (1)$$

and the respective intensity variance value V is determined according to formula (2) below:

$$V = \frac{1}{n-1}\sum_{i=1}^{n}(x_i - \bar{x})^2, \quad (2)$$

where the variable $$\sum_{i=1}^{n}(x_i - \bar{x})^2$$

is preferably determined according to formula (3)

$$\sum_{i=1}^{n}(x_i - \bar{x})^2 = \sum_{i=1}^{n} x_i^2 - n\bar{x}^2 \quad (3)$$

or according to formula (3') below:

$$\sum_{i=1}^{n}(x_i - \bar{x})^2 = \sum_{i=1}^{n} x_i^2 - \frac{1}{n}\left(\sum_{i=1}^{n} x_i\right)^2 \quad (3')$$

where $x_i$ denotes the intensities sensed within the respective scanning time interval, and n denotes a whole number, greater than 1, that indicates the number of intensities $x_i$ sensed within the respective scanning time interval.

7. The method according to claim 6, wherein the quotient of the intensity variance value V and the intensity mean value $\bar{x}$ is determined as an evaluation image point signal.

8. The method according to claim 6, wherein the number of photons $N_{ph}$ from the respective specimen point that are detected within the associated scanning time interval is determined, as an evaluation image point signal, as a function of the intensity mean value $\bar{x}$ and the intensity variance value V according to formula (4) below:

$$N_{ph} = \frac{\bar{x}^2}{V}. \quad (4)$$

9. A device for scanning-microscopy imaging of a specimen, comprising:

a scanning unit (12, 18) that is embodied to scan a plurality of specimen points by means of a scanning beam (14) in successive predetermined scanning time intervals, a sensing unit (36, 38) that is embodied to sense the intensity of the radiation emitted from the respectively scanned specimen point repeatedly within the associated scanning time interval, a calculation unit (40) that is embodied to determine an intensity mean value, as a mean value image point signal, from the intensities sensed in the respectively scanned specimen point, and an evaluation unit (42) that is embodied to assemble the mean value image point signals into a mean value raster image signal, wherein the calculation unit (40) is further embodied to additionally determine an intensity variance value, as a variance image point signal, from the intensities sensed in the respective sensed specimen point, and the evaluation unit (42) is further embodied to assemble the variance image point signals into a variance raster image signal.

10. The device according to claim 9, wherein the evaluation unit (42) is further embodied to generate an evaluation raster image signal on the basis of the mean value raster image signal and the variance raster image signal, and to assemble the generated evaluation image point signals into an evaluation raster image signal.

11. The device according to claim 8, wherein the sensing unit (36, 38) encompasses a digitizing means (38) that is embodied to digitize the intensity of the radiation detected within each scanning time interval n times in successive sub-intervals in order to sense n intensity values, n being a whole number greater than 1 and the sub-intervals each being equal to 1/n times the scanning time interval.

12. The device according to claim 11, wherein the digitizing means encompasses an analog-digital converter (38) that is embodied to sense the n intensity values by the fact that it converts an analog signal corresponding to the emitted radiation n times within the respective scanning time interval, in each case with a predetermined conversion time that is equal to the sub-interval, into a digital signal representing the respective intensity value.

13. The device according to claim 11, wherein the digitizing means encompasses a photon counter that is embodied to sense the n intensity values by the fact that it determines the number of photons that correspond to the emitted radiation n times within the respective scanning time interval, in each case with a predetermined counting time that is equal to the sub-interval.

14. The device according to claim 9, wherein the calculation unit (40) encompasses a freely programmable logic module, in particular an FPGA, a DSP, or an ASIC.

15. A confocal scanning microscope (10) having a device according to claim 9.

* * * * *